US006077975A

United States Patent [19]
Langer et al.

[11] Patent Number: 6,077,975
[45] Date of Patent: Jun. 20, 2000

[54] PROCESS FOR PREPARING DICYCLOALIPHATIC AMINES

[75] Inventors: Reinhard Langer, Tönisvorst; Gerd-Michael Petruck, Erkrath, both of Germany

[73] Assignee: Bayer Aktiengesellschaft, Leverkusen, Germany

[21] Appl. No.: 09/407,592

[22] Filed: Sep. 28, 1999

[30] Foreign Application Priority Data

Oct. 5, 1998 [DE] Germany .......................... 198 45 641

[51] Int. Cl.[7] ................................................. C07C 209/00
[52] U.S. Cl. ........................................... 564/450; 564/451
[58] Field of Search ..................... 564/450, 451

[56] References Cited

U.S. PATENT DOCUMENTS

| | | | |
|---|---|---|---|
| 4,952,549 | 8/1990 | Immel et al. | 324/330 |
| 4,960,941 | 10/1990 | Vedage et al. | 564/450 |
| 5,023,226 | 6/1991 | Immel et al. | 324/313 |
| 5,248,840 | 9/1993 | Immel et al. | 535/747 |
| 5,360,934 | 11/1994 | Vedage et al. | 564/451 |

OTHER PUBLICATIONS

P.N. Rylander, Catalytic Hydrogenation Over Platinum Metals, Academic Press (Month Unavailable), 1967, pp. 331–363, "Phenols and Phenyl Ethers" month unavailable.
Chem. Abstracts, vol. 71, Sep. 29–Oct. 20, 1969, Abstract #60838e, Ugine Kuhlmann & FR. 1,530,477, Jun. 28, 1968.
P.N. Rylander, Hydrogenation Methods, Academic Press, (Month unavailable), 1985, pp. 123–133 "Hydrogenation of Anilines, Phenols, and Derivatives".
Venkataraman Vishwanathan and Sankarasubbier Narayanan, J. Chem Soc. Chem Commun, (Month unavailable), 1990, pp. 78–80, "A Direct Correlation Between Dispersion, Metal Area, and Vapour Phase Hydrogenation of Aniline; A First Report".

*Primary Examiner*—Samuel Barts
*Attorney, Agent, or Firm*—Joseph C. Gil; Diderico van Eyle

[57] ABSTRACT

A low-pressure process for the hydrogenation of aromatic amines to give the corresponding symmetrical dicycloaliphatic amines in the presence of rhodium catalysts which are unmodified or modified by Ir, Ru, Os, Pd and/or Pt or mixtures of these metals, on supports modified by oxides of Cr, Mo, W, Mn and/or Re or mixtures of these oxides.

10 Claims, No Drawings

6,077,975

PROCESS FOR PREPARING DICYCLOALIPHATIC AMINES

FIELD OF THE INVENTION

The present invention relates to a low-pressure process for the hydrogenation of aromatic amines to give the corresponding symmetrical dicycloaliphatic amines in the presence of rhodium catalysts which are unmodified or modified by a noble metal selected from the group consisting of Ir, Ru, Os, Pd or Pt or mixtures of these metals, on supports modified by salts or oxides of the metals Cr, Mo, W, Mn and/or Re or mixtures of these salts or oxides.

BACKGROUND OF THE INVENTION

The catalytic hydrogenation of anilines to give the corresponding symmetrical dicycloaliphatic amines in the presence of noble metal catalysts is known. There exist only a few publications on the hydrogenation of anilines in the presence of noble metal catalysts at low pressure.

EP-A 0 324 983 and EP-A 0 324 984, herein incorporated by reference in their entirety, describe processes using basically modified catalysts which comprise both Ru and Pd. Whereas, in EP-A 0 324 983, considerable pressure is employed and only low dicyclohexylamine contents are achieved, EP-A 0 324 984 describes a low-pressure process having a high dicyclohexylamine yield. However, the catalysts having approximately 0.1–0.2 kg of starting material per liter of catalyst have only a low space velocity.

FR 1,530,477, herein incorporated by reference in its entirety, describes a low-pressure process in which aniline is reacted with large amounts of ammonia in a hydrogen stream in the presence of Pd supported catalyst at temperatures between 175 and 190° C. The product comprises large amounts of dicyclohexylamine.

EP-A 0 560 127, herein incorporated by reference in its entirety, describes a low-pressure process in which aniline is reacted in the presence of base-modified Ru—Pd supported catalysts. The catalysts have only a very low space velocity.

EP-A 0 208 933, herein incorporated by reference in its entirety, describes Rh catalysts on supports modified by Cr—Mn salts. The catalysts were developed for the dehydrogenation of precursors for o-phenylphenol synthesis at high temperatures.

EP-A 0 535 482, herein incorporated by reference in its entirety, likewise describes heat-stable Rh catalysts on supports modified by Cr—Mn salts for preparing o-phenylphenol, the catalysts comprising other nobel metals in addition to the Rh.

The Rh catalysts can be used for the dehydrogenation in thermostatic steady-state catalyst beds at low pressures and temperatures between 300 and 400° C.

U.S. Pat. No. 5,360,934, herein incorporated by reference in its entirety, discloses a process for hydrogenating aromatic amines in the presence of a rhodium catalyst which is applied to a support of κ-, θ- or δ-$Al_2O_3$. U.S. Pat. No. 4,960,941, herein incorporated by reference in its entirety, likewise discloses a process for hydrogenating aromatic amines in the presence of a rhodium catalyst. In this case, the rhodium catalyst is applied to a $TiO_2$ support. In both cases, the hydrogenation is carried out in the liquid phase under pressure.

Applications on the low-pressure hydrogenation of anilines using catalysts which comprise Rh as noble metal component are not known, although the literature reports that Rh catalysts are said to be suitable for low-pressure hydrogenations of anilines (P. N. Rylander, Catalytic Hydrogenation over Platinum Metals, Academic Press, 1967, pp. 331–363; P. N. Rylander, Hydrogenation Methods, Academic Press, 1985, pp. 123–133).

A prejudice against developing an Rh catalyst for producing dicyclohexylamines at low pressure was generated by a work published a few years ago on the gas phase hydrogenation of aniline in the presence of Rh on γ-$Al_2O_3$. Although increasing conversion rates were achieved with increasing Rh content of the catalyst at 1 atm and 200° C., the cyclohexylamine selectivity, at approximately 20%, is very low, regardless of the conversion rate. The dicyclohexylamine selectivity even decreases with increasing Rh content, and thus with increasing conversion rate, from 40% to 20%, so that predominantly unwanted products were obtained. (V. Vishwanathan, S. Narayanan, J. Chem. Soc., Chem. Commun., 1990, 78–80).

The publication suggests that rhodium catalysts are unsuitable, at low pressures in the gas phase, for the industrial hydrogenations of anilines to give cyclohexylamines and dicyclohexylamines.

The object underlying the present invention was to find a selective and high-space-velocity low-pressure process for the hydrogenation of aromatic amines, preferably of anilines, to give dicycloaliphatic amines, preferably dicyclohexylamines.

Surprisingly, it has been found that catalysts which comprise Rh on specially treated support materials are potent catalysts for implementing a process for the low-pressure hydrogenation of aromatic amines to give dicycloaliphatic amines.

SUMMARY OF THE INVENTION

The invention relates to a process for the hydrogenation of aromatic amines to give symmetrical dicycloaliphatic amines at pressures between 0.5 and 50 bar, the process comprising the step of hydrogenating an aromatic amine in the presence of a base-treated noble-metal supported catalyst, which comprises the support of the supported noble metal catalysts having been coated with salts or oxides of Cr, Mo, W, Mn and/or Re or mixtures of these salts or oxides, and the resultant support having been (i) activated by Rh as noble metal with or without an additional noble metal from the group consisting of Ir, Ru, Os, Pd and/or Pt, and (ii) treated with a base, wherein the base is wholly or partially neutralized by subsequent additional impregnation with a soluble acid. These and other features, aspects, and advantages of the present invention will become better understood with reference to the following description and appended claims.

DESCRIPTION OF THE INVENTION

Suitable starting compounds for the process according to the invention are aromatic amines as are described, for example, in DE 2 502 894 and U.S. Pat. No. 3,636,108, incorporated herein by reference in their entirety. Preference is given to aniline, $C_1$–$C_6$-alkylanilines and $C_1$–$C_6$-alkylated, possibly nucleus-alkylated, diaminobenzenes, aminonaphthalenes, $C_1$–$C_3$-alkylated aminonaphthalenes, diaminonaphthalenes and diaminodiphenyl-$C_1$–$C_3$ alkanes.

Those which may be mentioned are, for example, aniline, N-methylaniline, N-cyclohexylaniline, N-cyclohexylideneaniline, o-, m-, p-toluidine, 2,4-, 2,6-, 2,3-diamino-toluene, diphenylamine, 1- and 2-aminonaphthalene, 1,4-, 1,5-, 2,5-, 2,6-, 2,7-diaminonaphthalene and the isomeric diaminophenylmethanes.

Those which may be mentioned as preferred are, for example, aniline, N-cyclohexylaniline, N-cyclohexylideneaniline, o-, m-, p-toluidine, 2,4-, 2,6-, 2,3-diamino-toluene, diphenylamine.

Those which may be mentioned as particularly preferred are, for example, aniline, 2,4- and 2,6-diamino-toluene.

Very particularly preferably, the process according to the invention is used to hydrogenate aniline.

The anilines can be fed to the catalyst in the gaseous state, if appropriate, together with the monocyclic amine to be recycled. To produce dicyclohexylamines exclusively, the monocyclic amine is preferably recycled. The supported noble metal catalysts for the process according to the invention consist of a support which has been coated with a salt of the metals Cr, Mo, W, Mn or Re or mixtures of such salts. In addition, the supported noble metal catalysts comprise Rh as noble metal with or without, as additional noble metal component, a metal from the group consisting of Ir, Ru, Os, Pd and/or Pt.

Suitable supports for the supported noble metal catalysts of the process according to the invention are aluminas, $Al_2O_3$ in the various modifications ($\alpha$, $\kappa$, $\eta$, $\gamma$). Other supports otherwise suitable for noble metals include supports such as $TiO_2$, kieselguhr, silica gel, $BaCO_3$, $CaCO_3$, ZnO, MgO, pumice, $ZrO_2$, activated carbon and the oxides or oxidehydrates of metals of the group consisting of Cr, Mo, W, Mn and/or Re. Preferred supports include $TiO_2$, $BaCO_3$, MgO, $\gamma$-$Al_2O_3$ and the oxides or oxidehydrates of metals of the group consisting of Cr, Mo, W, Mn and/or Re, particularly preferably $\gamma$-$Al_2O_3$, the oxides or oxidehydrates of metals of the group consisting of Cr, Mo, W, Mn and/or Re, very particularly preferably $\gamma$-$Al_2O_3$.

The support can be used as a powder or in a piece-form as beads or as extrudates such as rings, wagon wheels and the like. Additionally, shaped bodies such as honeycombs or crossed-channel structures are useful.

Preferably, a support having a high BET surface area is used. The BET surface area should be above 50 $m^2$/g, preferably between 100 and 500 $m^2$/g, particularly preferably between 200 and 400 $m^2$/g.

If the support comprises oxides or oxidehydrates of metals of the group consisting of Cr, Mo, W, Mn and/or Re or mixtures of such oxides or oxidehydrates, if appropriate, the modification which is described below of the support prior to the application of the noble metal components can be dispensed with.

If a Cr—, Mo—, W—, Mn—and/or Re-free support is used, it must first be coated with one or more of these components. This can be achieved, for example, by impregnating or spraying the support with suitable salts of these elements. By drying and subsequently heating at temperatures of approximately 200 to 450° C., the salts applied are converted into compounds adhering on the support. The compounds of Cr, Mo, W, Mn and/or Re can, however, also be applied by co-precipitation of oxide hydroxide mixtures on the impregnated support using alkali metal hydroxides, alkaline earth metal hydroxides or ammonium hydroxides with or without subsequently extracting soluble fractions with water.

Particular preference is given to a uniform precipitation by slow release of the base by hydrolysis of a less basic precursor. Compounds which are particularly suitable for this purpose are ureas and urethanes, and urea is very particularly suitable.

The support thus pretreated is dried and then heated for between 10 minutes and 10 hours at 200 to 450° C., preferably 250 to 430° C., with the temperature also being able to be gradually increased within this range.

Suitable salts of Cr, Mo, W, Mn and/or Re are, for example, the acetates, nitrates, halides or sulfates. The water-soluble oxides of the higher oxidation states of Cr, Mo, W, Mn and/or Re oxides are likewise suitable.

Preferably, supports are used which have been pretreated with salts or oxides of Cr and Mn.

After the extraction of soluble compounds which may have been carried out and the drying and heating of the support modified by Cr, Mo, W, Mn and/or Re, the support is ready for absorption of the remaining active compounds.

The remaining active compounds are Rh with or without a noble metal selected from the group consisting of Ir, Ru, Os, Pd and/or Pt. The noble metals are applied in the form of solutions of their salts, for example in water. Salts which are suitable, for example, are halides, preferably chlorides, acetates, nitrates and acetylacetonates.

The support is treated with any suitable base, e.g. an alkali metal hydroxide or alkaline earth metal hydroxide, with or without alkali metal sulfate or alkaline earth metal sulfate. Suitable alkali metal hydroxides include NaOH or KOH, for example. Suitable alkaline earth metal hydroxide include $Mg(OH)_2$. As a sulfate component, $K_2SO_4$, for example, may be mentioned. The compounds can be applied individually or together by impregnation or spraying. Drying is carried out in between each impregnation step.

The alkali metal hydroxide or alkaline earth metal hydroxide can be applied prior to or after the treatment of the support by the noble metal components.

Preferably, Rh and, if appropriate, the noble metals for the modification are applied first, followed by the alkali metal hydroxide and, if appropriate, the alkali metal sulfate. If appropriate, a further impregnation with a base can follow.

After each impregnation with noble metal, if appropriate, reduction is carried out using hydrogen or another reducing agent. In each case, at the end of the last drying, reduction is carried out, using hydrogen, for example, at temperatures between 80 and 350° C.

After the reduction of the applied noble metals, the base present on the supported noble metal catalyst is completely or partially neutralized by impregnation with soluble acids which have a $pK_a$ less than 5 in water at 25° C.

Suitable soluble acids are the hydrohalic acids such as hydrochloric acid, organic acids such as acetic acid, formic acid or oxalic acid, and inorganic acids such as sulfuric acid or phosphoric acid.

For this purpose, between 0.1 and 10% by weight, preferably between 0.2 and 5% by weight, of acid are applied to the supported noble metal catalyst and the catalyst is then dried.

The finished supported noble metal catalyst comprises 0.1 to 10% by weight, preferably 0.3 to 3% by weight, of noble metal selected from the group consisting of Rh, Ir, Ru, Os, Pd and/or Pt, where between 100 and 30%, preferably between 100 and 70%, thereof are Rh. In addition, the supported noble metal catalyst comprises 0.05 to 5% by weight of Cr, Mo, W, Mn and/or Re, preferably Cr and Mn. In addition, the supported noble metal catalyst comprises 0.05 to 15% by weight of alkali metal ions or alkaline earth metal ions, 0.1 to 10% by weight of anions of acidic compounds which, dissolved in water at 25° C., have a $pK_a$ less than 5, and, if appropriate, 0.05 to 3% by weight of sulfur in the form of compounds such as alkali metal sulfates, alkaline earth metal sulfates, preferably potassium sulfate.

Preferably, in the process according to the invention, suitable supported noble metal catalysts are used in piece form in the form of fixed beds. The beds can be adiabatic or can be thermostated by using tube bundles through which, or around which, heat carrier flows. A combination of thermostated and adiabatic beds is also advantageous, or a succession of adiabatic reactors with coolers connected in between. The design of suitable reactors for such beds is part of the prior art and known to those skilled in the art.

The reaction can take place such that aniline and hydrogen, for example, if appropriate together with compounds to be recycled such as hydrogen, ammonia, cyclohexylamine, are heated, the heated mixture is run over the catalyst, some of the condensable compounds are precipitated by cooling and are ejected together with liquid possibly already present, a portion of the remaining gas stream is branched off for ejecting inert compounds and the remainder is returned to the reaction by compression. A gaseous starting material mixture is fed to the reactor.

The process according to the invention is carried out at temperatures between 50 and 250° C., preferably between 100 and 200° C., particularly preferably between 140 and 180° C.

The reaction takes place in a pressure range between 0.5 and 50 bar, preferably between 0.7 and 15 bar, particularly preferably between 0.9 and 8 bar.

The aromatic amine to be reacted can be reacted with hydrogen in a molar ratio between 1/500 and 1/5, preferably between 1/200 and 1/10, particularly preferably between 1/150 and 1/40.

Together with the aromatic amines and the hydrogen, small amounts of ammonia can be run over the catalyst. Ammonia decreases the reaction rate markedly and decreases the dicyclohexylamine selectivity only relatively slightly.

The space velocity of the catalysts in the process according to the invention can be between 0.1 and 5 kg, preferably between 1 and 2 kg, of aromatic amine per liter of catalyst an hour.

The selectivities with respect to dicycloaliphatic amines in the process according to the invention are markedly greater than 95%.

The process according to the invention makes it possible to convert aromatic amines into dicycloaliphatic amines with high selectivity in low-pressure apparatuses of little complexity.

The invention is further described in the following illustrative examples in which all parts and percentages are by weight unless otherwise indicated.

EXAMPLES

Example 1 (catalyst preparation)

1 l of γ-$Al_2O_3$ from Rhone-Poulenc (SPH 501, beads, Ø=4–6 mm, BET surface area approximately 350 $m^2$/g) was impregnated with 320 ml of a solution of 30.1 g of $MnSO_4H_2O$, 22.3 g of $(NH_4)_2Cr_2O_7$ and 164 g of urea. The impregnated support was agitated for 1 h at 90° C. in a saturated water vapor atmosphere. Two extractions each with 160 ml of water were then carried out to remove soluble compounds. The resulting support was dried and then heated for 30 minutes at 300° C. in a rotating drum.

20.3 g of $RhCl_3$ in 360 ml of water were applied by impregnation and the catalyst precursor was then dried at 110° C.

320 ml of a solution of 24 g of NaOH and 24 g of $K_2SO_4$ in water were then applied.

The catalyst was dried and activated for 3.5 h at 160° C. in a hydrogen stream.

The catalyst comprises 8 g of Rh, 9.2 g of Cr, 9.8 g of Mn, 24 g of NaOH and 24 g of $K_2SO_4$ per liter.

The catalyst was then impregnated with a solution of 58 g of $H_3PO_4$ in 220 g of water and dried for 3 h at 120° C. in a nitrogen stream.

Example 2

Table 1 shows that the catalyst from Example 1 hydrogenates aniline to give dicyclohexylamine at very high space velocities of approximately 1.6 kg/l×h over long periods of time at a high conversion rate and with high selectivity.

The experiment was carried out in an oil-thermostated metal tube having a diameter of the cylindrical catalyst bed of approximately 14 mm. The hydrogen/aniline mixture was fed in the gaseous state.

TABLE 1

Aniline hydrogenation, 164° C. oil temperature, 4 atm, $H_2$ stream. Catalyst: 50 ml of catalyst from Example 1.

| $H_2$/aniline mol/mol | Space velocity kg/l × h | ANI % | CHA % | DCA % | Benzene % | LB % | UC % | Service life h |
|---|---|---|---|---|---|---|---|---|
| 40 | 1.64 | 0 | 39.2 | 58.1 | 2.7 | 0 | 0 | 20 |
| 40 | 1.64 | 0 | 36.1 | 61.4 | 2.5 | 0 | 0 | 145 |
| 40 | 1.64 | 0 | 38.1 | 59.9 | 2.0 | 0 | 0 | 310 |
| 40 | 1.64 | 0 | 37.7 | 60.4 | 1.9 | 0 | 0 | 480 |

The catalyst is particularly suitable for industrial dicyclohexylamine production, because it can, in addition, be regenerated by burning off and reducing with hydrogen. ANl=aniline, CHA=cyclohexylamine, DCA=dicyclohexylamine, UC=unknown components, LB=low boilers (compounds which have a lower boiling point than benzene).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the hydrogenation of aromatic amines to give symmetrical dicycloaliphatic amines at pressures between 0.5 and 50 bar, the process comprising the step of hydrogenating an aromatic amine in the presence of a base-treated noble-metal supported catalyst, which comprises the support of the supported noble metal catalysts having been coated with salts or oxides of Cr, Mo, W, Mn and/or Re or mixtures of these salts or oxides, and the resultant support having been (i) activated by Rh as noble metal with or without an additional noble metal from the group consisting of Ir, Ru, Os, Pd and/or Pt, and (ii) treated with a base, wherein the base is wholly or partially neutralized by subsequent additional impregnation with a soluble acid.

2. The process of claim 1, wherein the step of hydrogenating the aromatic amine is carried out in the presence of a base-treated noble-metal supported catalyst consisting of 0.1 to 10% by weight of a noble metal component comprising a member selected from the group consisting of Rh, Ir, Ru, Os, Pd and Pt, wherein the noble metal component comprises between 100 and 30% of Rh.

3. The process of claim 1, wherein the step of hydrogenating the aromatic amine is carried out in the presence of a base-treated noble-metal supported catalyst comprising, in addition to the noble metal, 0.05 to 5% by weight of a component comprising a member selected from the group consisting of Cr, Mo, W, Mn and Re, 0.05 to 15% by weight of a member selected from the group consisting of alkali metal ions and alkaline earth metal ions, 0.1 to 10% by weight of anions of acidic compounds, which when dissolved in water at 25° C., have a $pK_a$ less than 5.

4. The process of claim 3, wherein the step of hydrogenating the aromatic amine is carried out in the presence of a base-treated noble-metal supported catalyst comprising further 0.05 to 3% by weight of sulfur in the form of compounds.

5. The process of claim 1, wherein the step of hydrogenating the aromatic amine is carried out at a space velocity that is between 0.1 and 5 kg of aromatic amine per liter of supported noble metal catalyst an hour.

6. The process of claim 1, wherein the step of hydrogenating the aromatic amine in the presence of a base-treated noble-metal supported catalyst occurs in a reactor and wherein a gaseous starting material mixture is fed to the reactor.

7. The process of claim 1, wherein the step of hydrogenating the aromatic amine in the presence of a base-treated noble-metal supported catalyst occurs with a selectivity that is greater than about 95%.

8. The process of claim 1, wherein the step of hydrogenating the aromatic amine in the presence of a base-treated noble-metal supported catalyst comprising a component selected from the group consisting of aluminas, $Al_2O_3$, $TiO_2$, kieselguhr, silica gel, $BaCO_3$, $CaCO_3$, ZnO, MgO, pumice, $ZrO_2$, activated carbon, Cr oxides, Mo oxides, W oxides, Mn oxides, Re oxides, Cr oxidehydrates, Mo oxidehydrates, W oxidehydrates, Mn oxidehydrates and Re oxidehydrates.

9. The process of claim 1, wherein the step of hydrogenating an aromatic amine occurs in the presence of a base-treated noble-metal supported catalyst that has been treated with a base comprising a member selected from alkali metal hydroxides and alkaline earth metal hydroxides.

10. The process of claim 9, wherein the step of hydrogenating an aromatic amine occurs in the presence of a base-treated noble-metal supported catalyst that has further been treated with a component comprising a member selected from the group consisting of alkali metal sulfates and alkaline earth metal sulfates.

\* \* \* \* \*